United States Patent [19]
Ozawa et al.

[11] 4,264,606
[45] Apr. 28, 1981

[54] INSECTICIDAL AND ACARICIDAL PHENYLCYCLO-PROPANE CARBOXYLIC ACID DERIVATIVES AND INSECTICIDAL AND ACARICIDAL COMPOSITIONS THEREOF

[75] Inventors: Kiyomi Ozawa; Shigeru Ishii, both of Funabashi; Mamoru Hayashi, Shiraoka; Masayoshi Hirose, Shiraoka; Ryoichi Nonaka, Shiraoka, all of Japan

[73] Assignee: Nissan Chemical Industries Ltd., Tokyo, Japan

[21] Appl. No.: 94,952

[22] Filed: Nov. 16, 1979

[30] Foreign Application Priority Data

Dec. 11, 1978 [JP]  Japan ............................. 53/152838

[51] Int. Cl.³ ................. A01N 43/40; C07D 213/55; C07D 213/57
[52] U.S. Cl. ...................... 424/263; 546/14; 546/300; 546/301; 546/302; 560/102; 560/59; 560/124; 260/465 D
[58] Field of Search ................ 546/14, 300, 301, 302; 560/59, 102; 424/263

[56] References Cited

U.S. PATENT DOCUMENTS

| | | | |
|---|---|---|---|
| 3,666,789 | 5/1972 | Itaya et al. | 560/102 |
| 3,835,176 | 9/1974 | Matsuo et al. | 560/102 |
| 4,163,787 | 8/1979 | Malhotra et al. | 546/302 |

FOREIGN PATENT DOCUMENTS

1235340  5/1960  France ......................... 560/59

*Primary Examiner*—Robert T. Bond

*Attorney, Agent, or Firm*—Oblon, Fisher, Spivak, McClelland & Maier

[57] ABSTRACT

Phenylcyclopropane carboxylic acid derivatives having the formula

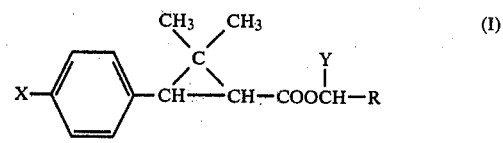

wherein X represents hydrogen or a halogen atom, $C_{1-5}$ alkyl group $C_{1-5}$ alkoxy group, trifluoromethyl, cyclopropyl, tri-lower alkylsilyl, lower alkylthio or cyano group; Y represents hydrogen atom or cyano group; and R represents

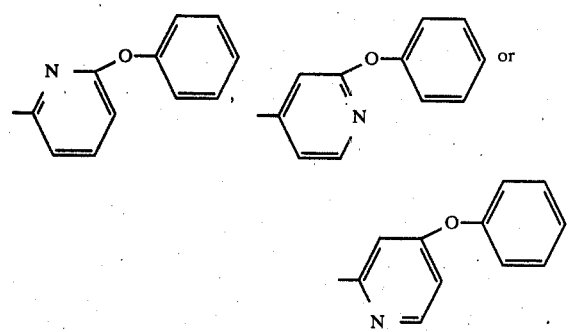

are novel compounds which are useful as insecticides and acaricides.

7 Claims, No Drawings

INSECTICIDAL AND ACARICIDAL PHENYLCYCLO-PROPANE CARBOXYLIC ACID DERIVATIVES AND INSECTICIDAL AND ACARICIDAL COMPOSITIONS THEREOF

BACKGROUND OF THE INVENTION

1. Field of the Invention

The present invention relates to novel compounds which have excellent insecticidal and acaricidal activities to various insect pests in sanitation as well as agriculture, horticulture and forest.

2. Description of the Prior Art

Recently, structure modifications and natural pyrethrin have been widely studied and various pyrethroids have been developed and used as insecticides.

The inventors have studied on syntheses and biochemical activities of various compounds for developing various compounds having insecticidal and acaricidal activities which are superior to the known compounds.

Heretofore, certain phenylcyclopropane carboxylic acid derivatives have been known.

The compounds having the formula

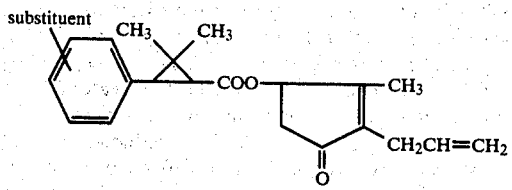

have been known in Collection of Czechoslovak Chemical Communication, 24, 2460 (1959) and 25, 1815 (1960).

These compounds are substituted cyclopropane carboxylic acid esters of allethrolon alcohol. However, insecticidal activity of the compounds for houseflies is only similar to that of allethrin of one of the commerciallized pyrethroids when the substituent on the phenyl group is a hydrogen atom and the insecticidal activity is inferior when the substituent on the phenyl group is chlorine, or fluorine atom or methyl or methoxy group. No acaricidal activity is described.

The compounds having the formula

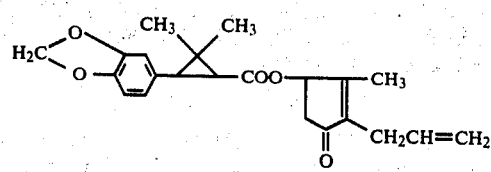

has been disclosed in Bochu Kagaku Vol. 27, III, page 51 (1962). However, the insecticidal activity of the compound is only similar to that of allethrin.

The inventors have checked a phenylcyclopropane carboxylic acid ester illustrated below.

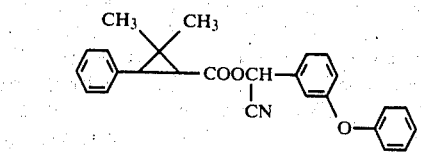

This compound has no substituent on phenyl group. However, an insecticidal and acaricidal activity of this compound is quite low.

The inventors have studied on syntheses and biochemical activities of various compounds so as to develop compounds having insecticidal and acaricidal activities superior to those of the known compounds.

It is important to obtain an insecticidal compound having highly insecticidal and acaricidal effects and widely used for controlling insect pests in sanitation as well as agriculture, horticulture and forest.

SUMMARY OF THE INVENTION

It is an object of the present invention to provide novel insecticidal and acaricidal compounds which have high insecticidal and acaricidal effects and low toxicity to mammals and fishes.

It is another object of the present invention to provide a process for producing novel insecticidal and acaricidal compounds which have excellent insecticidal and acaricidal activities to various insect pests in sanitation such as houseflies and mosquito as well as agriculture, horticulture and forest and which have wide insecticidal spectrum.

Briefly, the foregoing and other objects of the present invention have been attained by providing insecticidal and acaricidal compounds of phenylcyclopropane carboxylic acid derivatives having the formula

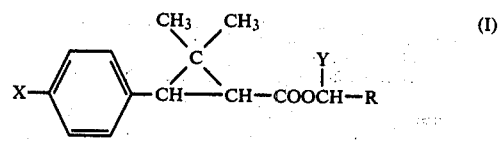

wherein X represents hydrogen or a halogen atom, $C_{1-5}$ alkyl group, $C_{1-5}$ alkoxy group, trifluoromethyl; cyclopropyl, tri-lower alkylsilyl, lower alkylthio or cyano group; Y represents hydrogen atom or cyano group; and R represents

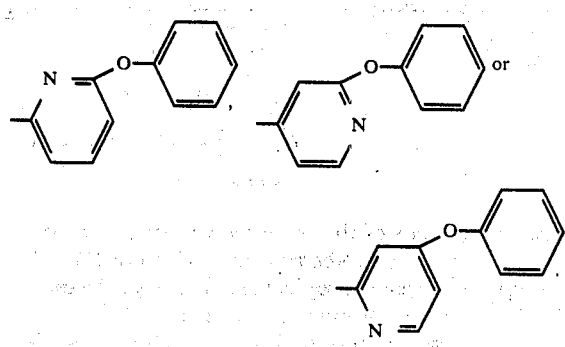

DETAILED DESCRIPTION OF THE PREFERRED EMBODIMENTS

The novel compounds of phenylcyclopropane carboxylic acid derivatives having the formula (I) have excellent insecticidal and acaricidal effect. The insecticidal and acaricidal activity of the insecticidal and acaricidal compounds of the present invention is significantly superior to that of allethrin as one of the commerciallized pyrethroids.

It is an unexpected result from the conventional knowledge that the compounds of the present invention have excellent insecticidal and acaricidal activity.

The process for producing the novel compounds will be illustrated by the following schemes.

In the schemes (A) to (D), the references X, Y and R are defined above Z represents a halogen atom or sulfonate group and Hal represents a halogen atom.

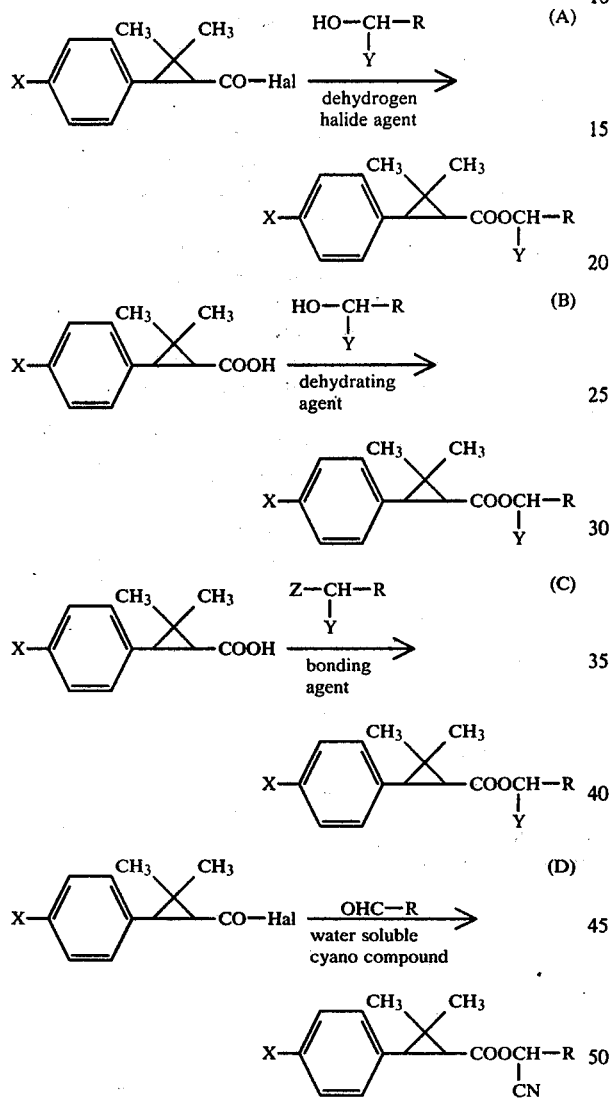

The compounds of the present invention can be obtained in high yield by the processes of (A) to (C).

When Y is a cyano group in the formula (I), the compound can be also obtained by the process (D).

The processes are further illustrated in detail as follows.

In the process (A), an organic tertiary base such as pyridine and triethylamine or an inorganic base such as alkali metal or alkaline earth metal hydroxides is used as the dehydrogen halide agent and the starting materials are reacted in an inert solvent such as benzene.

In the process (B), the starting components are reacted in an inert solvent such as acetonitrile in the presence of a dehydrating agent such as dicyclohexylcarbodiimide. Alternatively, p-toluene-sulfonic acid or conc-sulfuric acid used in an esterification can be used as the catalyst.

In the process (C), the starting materials are reacted in a solvent such as dimethylformamide, preferably under refluxing. In the course of the reaction, an alkali metal or alkaline earth metal hydroxide is used for converting an acid to a salt such as potassium or sodium salt etc.

In the process (D), the starting materials are reacted in an aprotic solvent which is not miscible to water such as n-heptane in the presence of water soluble cyan compound such as sodium cyanate and a phase transfer catalyst such as tetra-n-butyl ammonium chloride or trimethyl benzylammonium chloride to obtain the compound of the present invention in high yield.

Certain examples of syntheses of the compounds of the present invention will be illustrated below.

PREPARATION 1

6-Phenoxy-α-picolyl trans-2,2-dimethyl-3-(p-methoxyphenyl)-cyclopropane carboxylate (Compound No. 1)

Into 20 ml. of benzene, 2.0 g. of 6-phenoxy-α-picolyl alcohol and 0.8 g. of pyridine were dissolved. The solution was stirred under cooling with ice and 2.2 g. of trans-2,2-dimethyl-3-(p-methoxyphenyl)-cyclopropane carboxylic acid chloride was added dropwise to the solution. After reacting them for 1 hour, the reaction product was washed twice with 10 ml. of water and the organic layer was dried over anhydrous sodium sulfate and benzene was distilled off under a reduced pressure. The residual oily product was purified by a column chromatography (alumina: developing solvent: benzene) to obtain 3.6 g. of the object compound.

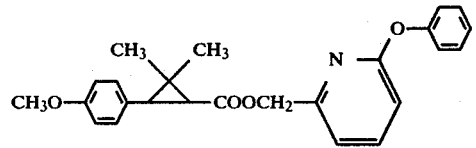

| Elementary Analysis: | C(%) | H(%) | N(%) |
|---|---|---|---|
| Found | 74.87 | 6.15 | 3.51 |
| Calculated | 74.42 | 6.25 | 3.47 |

NMR spectrum: δppm, $CCl_4$; 0.90(3H, s); 1.32(3H, s); 1.88(1H, d, J=6.0 Hz); 2.60(1H, d,J=6.0 Hz); 3.62(3H, s); 5.00(2H, s); 6.72(1H, d,J=8.0 Hz); 7.87(1H, dd,J=8.0 Hz); 6.70–7.40(10H, m).

PREPARATION 2

6-Phenoxy-α-picolyl trans-2,2-dimethyl-3-(p-t-butylphenyl)cyclopropane carboxylate (Compound No. 2)

Into 20 ml. of benzene, 2.0 g. of 6-phenoxy-α-picolyl alcohol and 0.8 g. of pyridine were dissolved. The solution was stirred under cooling with ice and 2.6 g. of trans-2,2-dimethyl-3-(p-t-butylphenyl)-cyclopropane carboxylic acid chloride was added dropwise to the solution. After reacting them for 1 hour, the reaction product was washed twice with 10 ml. of water and the organic layer was dried over anhydrous sodium sulfate and benzene was distilled off under a reduced pressure. The residual oily product was purified by a column chromatography (alumina; developing solvent: benzene) to obtain 4.1 g. of the object compound.

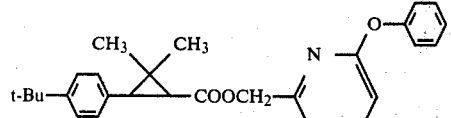

| Elementary Analysis: | C(%) | H(%) | N(%) |
| --- | --- | --- | --- |
| Found | 79.15 | 7.08 | 3.20 |
| Calculated | 78.29 | 7.27 | 3.26 |

NMR spectrum: δppm. CCl₄; 0.91(3H, s); 1.27(9H, s); 1.35(3H, s); 1.93(1H, d.J=6.0 Hz); 2.62(1H, d.J=6.0 Hz); 5.00(2H, s); 6.68(1H, d,J=8.0 Hz); 7.59(1H, d,J=8.0 Hz); 6.80–7.40(10H, m).

PREPARATION 3

Cyano(6-phenoxy-2-pyridyl)methyl trans-2,2-dimethyl-3-(p-t-butylphenyl)cyclopropane carboxylate (Compound No. 3)

Into 20 ml. of benzene, 2.3 g. of cyano(6-phenoxy-2-pyridine)methanol and 0.8 g. of pyridine were dissolved. The solution was stirred under cooling with ice and 2.7 g. of trans-2,2-dimethyl-3-(p-t-butylphenyl)-cyclopropane carboxylic acid chloride was added dropwise to the solution. After reacting them for 1 hour, the reaction product was washed twice with 10 ml. of water and the organic layer was dried over anhydrous sodium sulfate and benzene was distilled off under a reduced pressure. The residual oily product was purified by a column chromatography (alumina; developing solvent: benzene) to obtain 4.6 g. of the object compound.

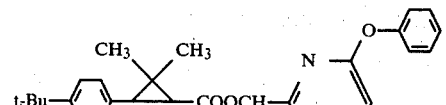

| Elementary Analysis: | C(%) | H(%) | N(%) |
| --- | --- | --- | --- |
| Found | 77.47 | 6.48 | 6.05 |
| Calculated | 76.63 | 6.65 | 6.16 |
| $n_D^{20}$ 1.5595 | | | |

NMR spectrum: δppm, CCl₄; 0.95(3H, bs); 1.28(9H, s); 1.30(1.5H, s); 1.38(1.5H, s); 2.06(1H, d.J=6.0 Hz); 2.15(1H, m); 6.37(1H, m), 6.91(1H, d.J=8.0 Hz); 7.80(1H, dd,J=8.0 Hz); 7.0–7.50(10H, m).

PREPARATION 4

Cyano(6-phenoxy-2-pyridyl)methyl trans-2,2-dimethyl-3-(p-trifluoromethylphenyl)-cyclopropane carboxylate (Compound No. 4)

Into 20 ml. of n-heptane, 2 g. of 6-phenoxy-α-picolinic aldehyde, 2.8 g. of trans-2,2-dimethyl-3-(p-trifluoromethylphenyl)-cyclopropane carboxylic acid chloride, 0.6 g. of sodium cyanide, 1.5 ml. of water and 0.1 g. of tetra-n-butylammonium chloride were added. The mixture was vigorously stirred at room temperature to react them for 40 hours. After the reaction, the precipitate was separated by filtration. The filtrate was washed with an aqueous solution of sodium bicarbonate, with an aqueous solution of sodium bisulfite and then, with water, and the organic layer was dried over anhydrous sodium sulfate and n-heptane was distilled off under a reduced pressure. The residual crude product was purified by a column chromatography (alumina; developing solvent: benzene) to obtain 4.4 g. of the object compound.

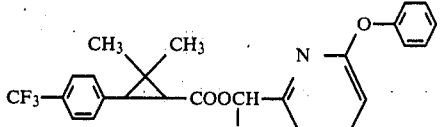

| Elementary Analysis: | C(%) | H(%) | N(%) |
| --- | --- | --- | --- |
| Found | 69.65 | 4.66 | 5.83 |
| Calculated | 69.95 | 4.56 | 6.00 |
| Refractive index: $n_D^{20}$ 1.5450 | | | |

PREPARATION 5

Cyano(2-phenoxy-4-pyridyl)methyl trans-2,2-dimethyl-3-(p-chlorophenyl)cyclopropane carboxylate (Compound No. 19)

Into 20 ml. of n-hexane, 2 g. of 2-phenoxy-α-picolinic aldehyde, 2.4 g. of trans-2,2-dimethyl-3-(p-chlorophenyl)cyclopropane carboxylic acid chloride, 0.6 g. of sodium cyanide, 1.5 ml. of water and 0.1 g. of trimethylbenzylammonium chloride were added. The mixture was vigorously stirred at room temperature to react them for 40 hours. After the reaction, 100 ml. of ethyl ether was added. The organic layer was washed with an aqueous solution of sodium bisulfite and with water and dried over anhydrous sodium sulfate and n-hexane was distilled off to obtain a crude ester. The crude ester was purified by a column chromatography (alumina; developing solvent: benzene) to obtain 3.6 g. of the object compound.

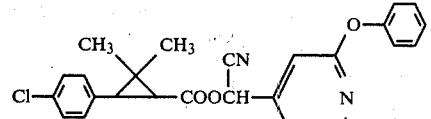

| Elementary Analysis: | C(%) | H(%) | N(%) |
| --- | --- | --- | --- |
| Found | 70.05 | 4.68 | 5.30 |
| Calculated | 69.36 | 4.89 | 6.47 |
| Refractive index: $n_D^{20}$ 1.5704 | | | |

PREPARATION 6

Cyano(6-phenoxy-2-pyridyl)methyl trans-2,2-dimethyl-3-(p-sec-butylphenyl)cyclopropane carboxylate (Compound No. 27)

Into 20 ml. of n-hexane, 2 g. of 6-phenoxy α-picolinic aldehyde, 2.6 g. of trans-2,2-dimethyl-3-(p-sec-butylphenyl)-cyclopropane carboxylic acid chloride, 0.6 g. of sodium cyanide, 1.5 ml. of water and 0.1 g. of tetrabutylammonium chloride were added. In accordance with the process of Preparation 5, the mixture was reacted and worked up to obtain a crude ester. The crude product was purified by a column chromatography (alumina; developing solvent: n-hexane) to obtain 3.6 g. of the object compound.

[Structure diagram: CH₃·CH₂·CH(CH₃)— phenyl —C(CH₃)(CH₃)cyclopropane—COOCH(CN)—(6-phenoxy-2-pyridyl)]

| Elementary Analysis: | C(%) | H(%) | N(%) |
|---|---|---|---|
| Found | 76.95 | 6.31 | 6.09 |
| Calculated | 76.63 | 6.65 | 6.16 |
| Refractive index: $n_D^{23.5}$ 1.5497 | | | |

PREPARATION 7

6-Phenoxy-α-picolyl 2,2-dimethyl 3-(p-cyclopropylphenyl)cyclopropane carboxylate (Compound No. 30)

In to 20 ml. of benzene, 2.0 g. of 6-phenoxy-α-picolyl alcohol and 1 g. of pyridine were dissolved. The solution was stirred under cooling with ice and 2.5 g. of 2,2-dimethyl-3-(p-cyclopropylphenyl)cyclopropane carboxylic acid chloride was added dropwise to the solution. After the addition, the reaction was continued further for 1 hour, and the reaction product was washed twice with 10 ml. of water and the organic layer was dried over anhydrous sodium sulfate and then benzene was distilled off under a reduced pressure. The resulting crude ester was purified by a column chromatography (alumina: developing solvent: benzene) to obtain 3.8 g. of the object compound ($n_D^{21.5}$=1.5807).

NMR spectrum: δppm, CCl₄: 0.5–1.0(4H, m); 0.88(3H, s); 1.31(3H, s); 1.5–2.0(1H, m); 1.92(1H, d,J=6.0 Hz); 2.64(1H, d,J=6.0 Hz); 4.99(2H, s); 6.65(1H, d,J=8.0 Hz); 6.80–7.30(10H, m); 7.48(1H, dd, J=8.0 Hz).

PREPARATION 8

Cyano(6-phenoxy-2-pyridyl)methyl 2,2-dimethyl-3-(p-trimethylsilylphenyl)cyclopropane carboxylate (Compound No. 31)

Into 20 ml. of benzene, 1.1 g. of α-cyano-6-phenoxy-2-picolyl alcohol and 0.5 g. of pyridine were dissolved. The solution was stirred under cooling with ice and 1.4 g. of 2,2-dimethyl-3-(p-trimethylsilylphenyl)cyclopropane carboxylic acid chloride was added dropwise to the solution. After the addition, the reaction was continued further for 1 hour and the reaction product was washed and dried and concentrated to obtain a crude ester in accordance with the Preparation 7. The crude ester was purified by a column chromatography (alumina: developing solvent: benzene) to obtain 2.1 g. of the object compound ($n_D^{21.5}$=1.5605).

NMR spectrum: δppm, CCl₄: 0.23(9H, s); 0.90(1.5H, s); 1.00(1.5H, s); 1.26(1.5H, s); 1.35(1.5H, s); 1.96(1H, d, J=6 Hz); 2.65(1H, m); 6.20(0.5H, s); 6.23(0.5H, s); 6.68(1H, d, J=8 Hz); 7.63 (1H, dd, J=8 Hz); 6.42–7.50(10H, m).

PREPARATION 9

Cyano(6-phenoxy-2-pyridyl)methyl 2,2-dimethyl-3-(p-trimethylsilylphenyl)cyclopropane carboxylate (Compound No. 31)

Into 20 ml. of n-hexane, 2 g. of 6-phenoxy-α-picolinic aldehyde, 2.8 g. of 2,2-dimethyl-3-(p-trimethylsilylphenyl)cyclopropane carboxylic acid chloride, 0.6 g. of sodium cyanide, 1 ml. of water and 0.1 g. of tetra n-butylammonium chloride were added. After the addition, the mixture was stirred and worked up as Paparation 8, to obtain 4.0 g. of the object compound. The physical properties of the resulting compound was corresponded with those of the compound obtained in Preparation 8.

PREPARATION 10

Preparation of Compound No. 3 ($[\alpha]_D^{20}$=+40.5)

Into 100 ml. of 60% ethanol aqueous solution, 4.8 g. of (±) trans-2,2-dimethyl-3-(p-t-butylphenyl)-cyclopropane carboxylic acid and 2.5 g. of (−)α-methylbenzylamine were added and dissolved by heating. The solution was kept at room temperature for one night and the precipitated crystals were separated by a filtration. The resulting crystals were recrystallized two times from an ethanol-aqueous solution and also recrystallized two times from ethyl acetate and further recrystallized from 60% ethanol-aqueous solution to obtain 2.2 g. of the crystals.

The crystals were decomposed in 10% sulfuric acid. The product was extracted with ether and dried over anhydrous sodium sulfate. Ether was distilled off to obtain 1.47 g. of trans-2,2-dimethyl-3-(p-t-butylphenyl)-cyclopropane carboxylic acid having (+) predominant optical rotary power ($[\alpha]_D^{20}$:+41.2 (CHCl₃) and melting point: 117°–119° C.).

In 10 ml. of benzene, 0.74 g. of the carboxylic acid and 0.39 g. of thionyl chloride were reacted at 50° C. to obtain 0.77 g. of the carboxylic acid chloride.

In accordance with the process of Preparation 4 except using the resulting acid chloride, the process for the production was repeated to obtain 0.2 g. of the Compound 3 ($[\alpha]_D^{20}$: +40.5 and $n_D^{20}$: 1.5597).

The Compound No. 3 ($[\alpha]_D^{20}$=+40.5) was tested in accordance with the test methods of Experiment 5 and 4 described below. The Percent mortalities of two spotted mite and carmine mite in the case of Compound No. 3 $[\alpha]_D^{20}$=+40.5 were superior to those of the Compound No. 3 (racemic form).

The other typical compounds produced in accordance with Preparation No. 1–10 will be described.

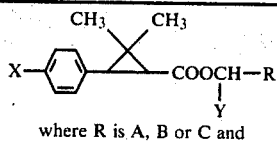

where R is A, B or C and

A is 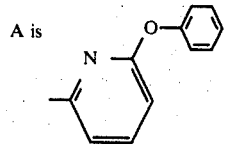

B is 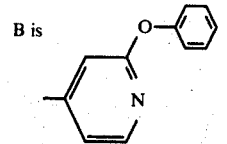

and C is 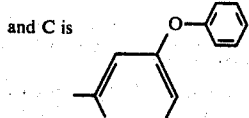

| Compound No. | Substituents in the formula X | Y | R | Refractive index $n_D$ (temp. °C.) |
|---|---|---|---|---|
| 5 | H | H | A | 1.5740 (20) |
| 6 | H | CN | A | 1.5665 (20) |
| 7 | Cl | H | A | 1.5760 (20) |
| 8 | Cl | H | B | 1.5739 (20) |
| 9 | Cl | H | C | 1.5719 (20) |
| 10 | Cl | CN | A | 1.5663 (20) |
| 11 | Cl | CN | C | 1.5801 (20) |
| 12 | Br | CN | A | 1.5784 (20) |
| 13 | CH$_3$ | H | A | 1.5766 (20) |
| 14 | CH$_3$ | H | B | 1.5801 (20) |
| 15 | CH$_3$ | H | C | 1.5719 (20) |
| 16 | CH$_3$ | CN | A | 1.5562 (20) |
| 17 | CF$_3$ | H | A | 1.5329 (20) |
| 18 | CF$_3$ | H | B | 1.5369 (20) |
| 19 | Cl | CN | B | 1.5704 (20) |
| 20 | t-Bu | CN | B | 1.5620 (20) |
| 21 | t-Amyl | CN | A | 1.5497 (23.5) |
| 22 | t-Amyl | H | A | 1.5595 (23.5) |
| 23 | n-Bu | CN | A | 1.5551 (23.5) |
| 24 | n-Bu | H | A | 1.5606 (23.5) |
| 25 | iso-Bu | CN | A | 1.5483 (23.5) |
| 26 | iso-Bu | H | A | 1.5547 (23.5) |
| 27 | sec-Bu | CN | A | 1.5497 (23.5) |
| 28 | sec-Bu | H | A | 1.5595 (23.5) |
| 29 | cyclopropyl | CN | A | 1.5700 (21.5) |
| 30 | cyclopropyl | H | A | 1.5807 (21.5) |
| 31 | (CH$_3$)$_3$Si— | CN | A | 1.5605 (21.5) |
| 32 | (CH$_3$)$_3$Si— | H | A | 1.5565 (21.5) |
| 33 | CH$_3$S— | CN | A | 1.5863 (20) |
| 34 | NC | CN | A | 1.5739 (20) |

The cyclopropane carboxylic acid derivatives of the present invention include, of course, optical isomers thereof due to the assymetric carbon atom of the carboxylic acid moiety and the alcohol moiety, and geometrical isomers thereof due to the stereo structure of the carboxylic acid moiety.

The insecticidal and acaricidal compounds of phenyl-cyclopropane carboxylic acid derivatives having the formula (I) are useful as insecticides for controlling insect pests in sanitation as well as agriculture, horticulture and forest, for example, the following injurious insects:

INSECTS INJURIOUS TO SANITATION house fly and pale house mosquito and blattella;

INSECTS INJURIOUS TO AGRICULTURE, HORTICULTURE AND FOREST

Rice:

rice stem borer, smaller brown planthopper, whitebacked planthopper, brown planthopper and green rice leafhopper;

Vegetables:

cabbage army worm, tobacco cutworm, common white, green peach aphid, diamondback moth and 28-spotted lady beetle;

Friuts:

smaller tea tortorix, comstock mealybug, european red mite, citrus red mite and two spotted spider mite;

The injurious insects to which the insecticidal compound of the present invention is applied, are not limited to the above-mentioned insects.

The insecticidal activity of the compounds (I) is imparted not only young larva but also old larva in direct or in penetration by direct contact or immersion. The compounds of the present invention are also effective to kill various acarina such as carmine mite (*Tetranychus cinnabarinus*), Kanzawa spider mite (*Tetranychus Kanzawai*), two-spotted mite (*Tetranychus urticae*), citrus red mite (*Panonychus citri*), Japanese citrus rust mite (*Aculus pelekassi*), European red mite (*Panonychus ulmi*), sweet cherry spider mite (*Tetranychus viennensis*) etc. and are also effective for the other plant parasitic acarina which cause damage to agricultural, horticultural plants and forests and are also applicable to various animal parasitic acarina and other acarina.

When the compound is used as an insecticidal or acaricidal composition, suitable adjuvant is admixed with the insecticidal compound at suitable ratio to dissolve, to disperse, to suspend, to blend, to immerse, to adsorb or to adhere the insecticidal compound so as to form suitable composition in a form of a solution, a dispersion, an emulsion, an oil spray, a wettable powder, a dust, a granule, a pellet, a paste or an aerosol.

The insecticidal or acaricidal composition incorporating the compound of the present invention as an active ingredient can be blended to suitable other agricultural composition, such as insecticides, acaricides, fungicides, fertilizers, plant nutritions and plant growth regulators which is applied in the same manner.

The insecticidal effect of the compound of the present invention can be improved by combining it with synergist such as piperonyl butoxide (P.B.) octachlorodipropyl ether or N-octyl bicycloheptene dicarboxyimide.

The stability of the compound of the present invention can be improved by combining an antioxident such as phenol type antioxidants e.g. 2,6-di-t-butyl-4-methylphenol (B.H.T.) and 2,6-di-t-butylphenol and amine type antioxidants.

In the preparation of the insecticidal or acaricidal compositions, suitable carriers include solid carriers such as clay, talc and bentonite; and liquid carriers such as water; alcohols e.g. methanol and ethanol; ketones, ethers, aliphatic hydrocarbons and aromatic hydrocarbons e.g. benzene, toluene, xylene; organic bases; acid amides e.g. dimethylformamide; esters; and nitriles. If desired, an additive is incorporated. Suitable additives include emulsifiers, dispersing agents, suspending agents, spreaders, penetrating agents and stabilizers. A quantity of the active ingredient in the composition can be selected as desired and usually in a range of 0.05 to 90 wt.% preferably 0.1 to 30 wt.% as a concentrated composition, which is used after diluting with water etc. In a form of an aerosol, a smudge a mosquito-repellent incense or an electric mosquito-repellent incense, a quantity of the active ingredient in the composition can be decreased to Certain insecticidal or acaricidal compositions containing the compound of the present invention will be illustrated as follows.

| COMPOSITION 1. Emulsifiable concentrate: | |
|---|---|
| Compound No. 4 | 25 wt. parts |
| Xylol | 30 wt. parts |
| Sorpol 2680·(Toho Chem.) | 15 wt. parts |
| Dimethylformamide | 30 wt. parts |

The components were uniformly mixed and diluted 50 times with the quantity of water and the aqueous solution was sprayed in amounts of 25 to 50 ml/m² or it was diluted with 1,000 to 5,000 times the quantity of water and the aqueous solution was sprayed in amounts of 100 to 800 liter/10 ares.

| COMPOSITION 2: Oil solution | |
|---|---|
| Compound No. 6 | 0.2 wt. parts |
| Piperonyl butoxide | 0.8 wt. parts |
| Kerosene | 99.0 wt parts |

The components were uniformly mixed to obtain an oily solution.

The oil solution was applied in amounts of 25 to 50 ml/m² to a floor or 5 to 10 ml/m² to a drain or a puddle.

| COMPOSITION 3: Dust: | |
|---|---|
| Compound No. 10 | 0.4 wt. parts |
| Piperonyl butoxide | 1.6 wt. parts |
| Talc. | 98 wt. parts |

The components were uniformly mixed to obtain a dust.

The dust was applied at a ratio of 15 g/m² or 3 to 4 Kg/10 ares.

| COMPOSITION 4: Wettable powder: | |
|---|---|
| Compound No. 3 | 10 wt. parts |
| Zeeklite | 85 wt. parts |
| Sorpol 8048 (Toho Chem.) | 3 wt. parts |
| Runox 1000 (Toho Chem.) | 2 wt. parts |

The components were uniformly ground and mixed to obtain a wettable powder. The wettable powder was diluted with 500 to 2000 times of water and it was sprayed in amounts of 50 to 800 liters/10 ares.

The similar compositions were prepared by substituting the active ingredient to the other compounds of the invention and were applied by the same manners.

The following is certain experiments which are conducted with the compositions of the present invention.

As references, the following active ingredients were used instead of the compound of the present invention.

Allethrin:

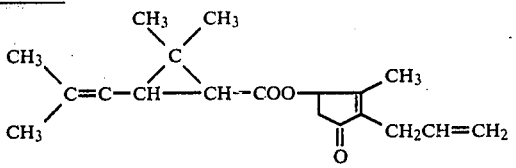

Tricyclohexyl tin-hydroxide:

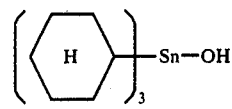

EXPERIMENT 1

Contact test for killing houseflies

A 1 cc quantity of 100 ppm and 10 ppm solution of each of the compounds of the present invention and the references in acetone was dropped onto the bottom of a Petri dish (9 cm), and was spread uniformly over the surface of the dish. Acetone was completely evaporated at room temperature. Ten adult houseflies were placed in the dish, which was covered with a plastic cover having many holes. The Petri dish was maintained in a constant temperature room at 25° C. for 24 hours and percent mortality of the houseflies was determined.

The test was repeated twice and the results are shown in Table 1.

TABLE 1

| Active ingredient | Concentration Percent mortality (%) | |
|---|---|---|
|  | 100 ppm | 10 ppm |
| 1 | 100 | 75 |
| 4 | 100 | 100 |
| 5 | 100 | 70 |
| 6 | 100 | 100 |
| 7 | 100 | 85 |
| 8 | 100 | 50 |
| 10 | 100 | 100 |
| 12 | 100 | 95 |
| 13 | 100 | 85 |
| 16 | 100 | 100 |
| 17 | 100 | 95 |
| 18 | 85 | — |
| 19 | 85 | — |
| 23 | 100 | 95 |
| 24 | 100 | — |
| 25 | 100 | — |
| 26 | 95 | — |
| 27 | 100 | — |
| 28 | 100 | — |
| 29 | 100 | 100 |
| 30 | 100 | 65 |
| 33 | 100 | — |
| 34 | 90 | — |
| Allethrin | 100 | 40 |

EXPERIMENT 2

Contact test for killing green rice leafhopper

Stems and leaves of a rice seedling were dipped in each emulsion of each of the composition of the compounds of the invention (100 ppm) for 10 seconds and were dried in air. The stems and leaves were covered with a glass cylinder and 15 of adults green rice leafhoppers were released into the cylinder which was covered with a cover having holes and was maintained in a constant temperature room at 25° C. for 24 hours or 48 hours and percent mortality was determined. The test was repeated two times. The results are shown in Table 2.

TABLE 2

| Active ingredient | Percent mortality (%) | |
|---|---|---|
| | after 24 hr. | after 48 hr. |
| 4 | 95 | 100 |
| 10 | 85 | 100 |
| 16 | 100 | 100 |
| 17 | 100 | 100 |

EXPERIMENT 3

Contact test for killing Tobacco cutworm

Leaves of cabbage were dipped in 100 ppm aqueous emulsion of the compound of the invention or the reference for 10 seconds. The leaves were taken up and dried in air and put in a Petri dish having a diameter of 7.5 cm. Ten of tobacco cutworm (third instar) were put in the Petri dish which was covered with a cover having many holes. The Petri dish was maintained in a constant temperature room at 25° C. for 24 or 48 hours and percent mortality was determined. The tests were carried out in two groups.

TABLE 3

| Active ingredient | Percent mortality (%) | |
|---|---|---|
| | after 24 hr. | after 48 hr. |
| 3 | 100 | 100 |
| 4 | 100 | 100 |
| 10 | 95 | 100 |
| 14 | 90 | 100 |
| 17 | 100 | 100 |
| 29 | 100 | 100 |

EXPERIMENT 4

Test for killing carmine mite

Leaves of kidney bean was cut by a leaf-punch in a form of circle having a diameter of 1.5 cm. The leaf-discs were put on a wet filter on a polystyrene cup. Ten of carmine mites were inoculated on the leaf-discs in the cup. Half days after the inoculation, each solution prepared by diluting each emulsifiable concentrate of the present invention or each control with a spreader (Nitten S 4,000 times manufactured by Nissan Chem.) at each predetermined concentration was sprayed by a rotary spray for 2 ml. per each cup.

Numbers of mortalities of carmine mites were measured after 24 hours or 48 hours from the spraying and percent mortalities were calculated.

The tests were carried out in two groups. The results were shown in Table 4.

TABLE 4

| Compound | Concentration (ppm) | Percent mortality (%) | |
|---|---|---|---|
| | | After 24 hr. | After 48 hr. |
| Compound 3 | 300 | 100 | 100 |
| | 90 | 100 | 100 |
| | 27 | 85 | 100 |
| | 8 | 80 | 90 |
| Compound 21 | 300 | 100 | 100 |
| | 90 | 90 | 100 |

TABLE 4-continued

| Compound | Concentration (ppm) | Percent mortality (%) | |
|---|---|---|---|
| | | After 24 hr. | After 48 hr. |
| | 27 | 60 | 95 |
| | 8 | 60 | 75 |
| | 300 | 85 | 100 |
| Compound 23 | 90 | 60 | 70 |
| | 300 | 100 | 100 |
| Compound 25 | 90 | 75 | 75 |
| | 300 | 100 | 100 |
| Compound 27 | 90 | 100 | 100 |
| | 300 | 85 | 100 |
| Compound 28 | 90 | 30 | 60 |
| | 300 | 100 | 100 |
| Compound 29 | 90 | 75 | 100 |
| | 300 | 100 | 100 |
| Compound 31 | 90 | 100 | 100 |
| | 300 | 100 | 100 |
| Compound 32 | 90 | 95 | 100 |
| | 300 | 100 | 100 |
| Compound 33 | 90 | 75 | 85 |
| | 300 | 90 | 100 |
| Tricyclohexyl tin-hydroxide | 90 | 50 | 80 |
| | 27 | 35 | 55 |
| | 8 | 10 | 20 |
| Non-treatment | — | 0 | 0 |

EXPERIMENT 5

Test for killing two spotted mites

In accordance with the method of Experiment 4, percent mortalities of two spotted mites were measured. The results are shown in Table 5.

TABLE 5

| Compound | Concentration (ppm) | Percent mortality (%) After 48 hr. |
|---|---|---|
| Compound 3 | 300 | 100 |
| | 90 | 80 |
| Compound 21 | 300 | 85 |
| Compound 23 | 300 | 80 |
| Compound 27 | 300 | 95 |
| Compound 28 | 300 | 70 |

EXPERIMENT 6

Residual test against two-spotted mites

In each pot having a diameter of 12 cm., kidney bean was grown and parasitic two-spotted mites were inoculated on a leaf. The natural proliferation of the mites were allowed for 8 days and then each solution prepared by diluting each emulsifiable concentrate of the present invention and each control with a spreader at each predetermined concentrate was sprayed by a spray to wet the leaves. After drying it in air, it was maintained in a green house. Numbers of mites were measured after the specific days. The parasitic acarina index was calculated by the equation.

$$\text{parasitic acarina index} = \frac{\text{number of parasitic acarina after spraying}}{\text{number of parasitic acarina before spraying}} \times 100$$

The results are shown in Table 6.

TABLE 6

| | | Test for controlling parasitic acarina | | | | |
|---|---|---|---|---|---|---|
| | | Parasitic acarina index | | | | |
| | Concentration | Two-spotted mite (days) | | | | |
| Compound | (ppm) | 3 | 7 | 11 | 18 | 24 |
| Compound No. 3 | 50 | 0 | 0 | 0 | 0 | 0 |
| Reference Tricyclohexyl tin-hydroxide | 50 | 8 | 0 | 0 | 3 | 3 |
| Non-treatment | — | 53 | 122 | 602 | 548 | 355 |

We claim:

1. A phenylcyclopropane carboxylic acid ester having the formula

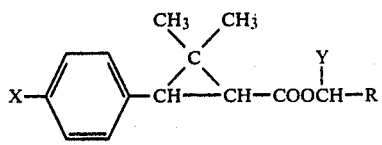  (I)

wherein X is halogen, $C_{1-5}$ alkyl group, trifluoromethyl, cyclopropyl or tri-lower alkylsilyl; Y is hydrogen or cyano; and R is

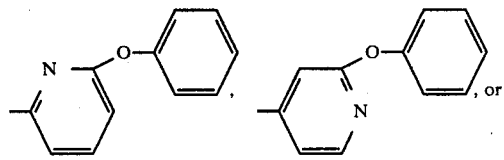, or

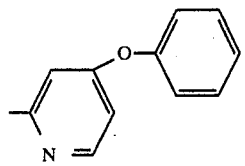

2. A phenylcyclopropane carboxylic acid ester according to claim 1, wherein X is halogen, a $C_{1-5}$ alkyl group or a trifluoromethyl group.

3. A phenylcyclopropane carboxylic acid ester according to claim 1, wherein X is cyclopropyl or tri-lower alkylsilyl.

4. A phenylcyclopropane carboxylic acid ester according to claim 1, wherein R is

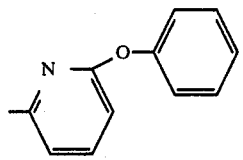

5. An insecticidal and acaricidal composition comprising an effective amount of a phenylcyclopropane carboxylic ester according to claim 1 and a suitable adjuvant in the form of a solution, a dispersion, an emulsifiable concentrate, an oil solution, a wettable powder, a dust, a granule, a tablet, a pellet, a paste, an aerosol, a smudge, or a mosquite-repellent incense.

6. An insecticidal and acaricidal composition according to claim 5 additionally containing a synergistically effective amount of a compound selected from the group consisting of piperonyl butoxide, octachlorodipropyl ether and N-octyl bicycloheptane dicarboxyimide.

7. An insecticidal and acaricidal composition according to claim 5 additionally containing an effective amount of an antioxidant.

* * * * *